United States Patent
Bashford et al.

(10) Patent No.: US 6,527,697 B2
(45) Date of Patent: Mar. 4, 2003

(54) METHOD FOR ALLEVIATING SYMPTOMS OF CERTAIN TYPES OF DISORDERS USING ELECTROMAGNETIC FIELDS

(75) Inventors: Grant Ernest Bashford, Reaboro (CA); Edward Paul Gerard Wessler, Baldwin (CA); Raymond Macklin Whitton, Toronto (CA)

(73) Assignee: MS Relief Ltd., Markham (CA)

(*) Notice: Subject to any disclaimer, the term of this patent is extended or adjusted under 35 U.S.C. 154(b) by 82 days.

(21) Appl. No.: 09/740,839

(22) Filed: Dec. 21, 2000

(65) Prior Publication Data

US 2002/0082465 A1 Jun. 27, 2002

(51) Int. Cl.[7] .................................................. A61N 1/06
(52) U.S. Cl. ........................................... 600/13; 600/15
(58) Field of Search ............................ 600/9, 10, 11, 600/13, 14, 15

(56) References Cited

U.S. PATENT DOCUMENTS

| | | | | |
|---|---|---|---|---|
| 435,376 A | * | 8/1890 | Brown | 600/13 |
| 4,428,366 A | * | 1/1984 | Findl et al. | 600/14 |
| 5,002,068 A | | 3/1991 | Powell | 128/846 |
| 5,047,005 A | | 9/1991 | Cadwell | 600/13 |
| 5,066,891 A | | 11/1991 | Harrold et al. | 315/8 |
| 5,170,094 A | | 12/1992 | Giannantonio et al. | 313/413 |
| 5,208,510 A | | 5/1993 | Grocki | 315/85 |
| 5,224,922 A | | 7/1993 | Kurtz | 600/9 |
| 5,441,495 A | * | 8/1995 | Liboff et al. | 300/13 |
| 5,465,012 A | | 11/1995 | Dunnam | 307/91 |
| 5,470,846 A | | 11/1995 | Sandyk | 519/159 |
| 5,518,495 A | | 5/1996 | Kolt | 600/13 |
| 5,586,064 A | | 12/1996 | Grupp | 364/572 |
| 5,669,868 A | | 9/1997 | Markoll | 600/14 |
| 5,788,624 A | * | 8/1998 | Lu et al. | 600/15 |
| 5,885,976 A | | 3/1999 | Sandyk | 519/159 |
| 6,128,174 A | | 10/2000 | Ritter et al. | 600/13 |
| 6,234,953 B1 | | 5/2001 | Thomas et al. | 600/14 |

OTHER PUBLICATIONS

Webpage printout, undated, www.walkerscientific.com/HelmholtzCoils/index.html.

Webpage printout, undated, www.link.lviv.ua/~vasya/ms-factor/magms.htm, O. Borodjuk et al, *Geomagnetic Field Affect Prevalence of Multiple Sclerosis: Preliminary Data*.

Webpage printout, undated, www.link.lviv.ua/~vasya/Ms-factor.html, O. Borodjuk et al, *Correlation Analysis Between Earth Magnetic Field and Multiple Sclerosis Prevalence*.

\* cited by examiner

Primary Examiner—Charles G. Freay
Assistant Examiner—Emmanuel Sayoc
(74) Attorney, Agent, or Firm—Bereskin & Parr

(57) ABSTRACT

A therapeutic device and the use of it to alleviate the symptoms of health-related disorders. The device includes a magnetic field generator capable of creating a magnetic field, a power supply for providing power to energize the generator to generate a generated magnetic field, and a controller coupled to the power source for varying the power provided by the power supply to the generator. A method of alleviating the symptoms of a health-related disorder includes the steps of determining the direction and strength of the predominant component of a local magnetic field, generating a first magnetic field within a zone, wherein the first magnetic field is opposite in direction to the predominant component, wherein the first magnetic field is of sufficient strength such that within the zone the resulting field is between approximately 10,000 nT and 30,000 nT or between approximately −10,000 nT and −30,000 nT (or of sufficient strength to provide therapeutic value) and positioning an individual having health-related disorder symptoms substantially within the zone for a period of time sufficient to alleviate the symptoms.

7 Claims, 8 Drawing Sheets

METHOD FOR ALLEVIATING SYMPTOMS OF CERTAIN TYPES OF DISORDERS USING ELECTROMAGNETIC FIELDS

FIELD OF THE INVENTION

This invention relates to the field of therapeutic devices, generally.

BACKGROUND OF THE INVENTION

Neurological disorders such as Multiple Sclerosis ("MS"), Guillain-Barre Syndrome, myotonic multiple dystrophy and endocrine system disorders can create a broad range of disabling symptoms caused by a disruption of the brain's ability to communicate with other parts of the body. These symptoms can include slurred speech, difficulty walking and impaired fine motor skills. Sometimes these disorders are caused by problems with a person's auto-immune system. As well, an individual's ability to function may also be impaired by the onset of migraine headaches.

Clinical depression, in general terms, is characterized by symptoms such as lack of energy, low self esteem, and prolonged feelings of sadness and hopelessness. Neurotransmitters are naturally occurring chemicals such as serotonin and dopamine, that carry electrical impulses within the brain. Sometimes these chemicals are too abundant or too scarce, causing the electrical impulses not to travel as effectively as they normally do. Chemical imbalances in the brain cause psychological disorders or mental illness such as clinical depression. Such conditions are sometimes referred to as "unipolar disorders" or mood disorders.

There is accordingly a need for apparatus which alleviates the symptoms of certain neurological, endocrinal, and auto-immune disorders.

SUMMARY OF THE INVENTION

The present invention is directed towards a therapeutic device, which has common, but by no means exclusive application to alleviating the symptoms of neurological, endocrinal, and auto-immune disorders such as Multiple Sclerosis, Guillain-Barre Syndrome, myotonic multiple dystrophy, migraine headaches and unipolar disorders. The applicants understand that the vertical component of the geomagnetic field adversely affects individuals suffering from health-related disorders such as these.

The subject device includes a magnetic field generator, a power supply for providing power to energize the generator to generate a generated magnetic field, and a controller coupled to the power source for varying the power provided by the power supply to the generator. Preferably, the device also includes a magnetic field sensor operatively coupled to the controller, wherein the controller is responsive to the magnetic field sensor. For some applications, the device is preferably sized such that the generated magnetic field is sufficiently large to envelop all or a significant portion of a person's body. For other applications, the generated magnetic field may be much smaller for more localized therapy such as to a person's hands, feet, joints or other parts of the human anatomy.

The invention is also directed towards the use of the present therapeutic device invention described above to alleviate the symptoms of health-related disorders including neurological, endocrinal, and auto-immune disorders such as Multiple Sclerosis, myotonic multiple dystrophy, migraine headaches and unipolar disorders.

As well, the invention is directed towards a method of alleviating the symptoms of health-related disorders. The method comprises the steps of:

A. determining the direction and strength of a predominant component of a local magnetic field;

B. generating a first magnetic field within a zone, wherein the generated magnetic field is approximately opposite in direction to the predominant component of the local magnetic field;

C. wherein the first magnetic field is of sufficient strength such that within the zone the strength of the resulting magnetic field has an absolute value between approximately 10,000 nT and 30,000 nT; and D. positioning an individual having health-related disorder symptoms substantially within the zone for a sufficient period of time to alleviate the individual's symptoms.

Preferably, step A. of the method includes sensing the strength of the predominant component and step B. includes varying the generated magnetic field in accordance with any detected changes in strength of the sensed predominant component.

BRIEF DESCRIPTION OF THE DRAWINGS

The present invention will now be described, by way of example only, with reference to the following drawings, in which like reference numerals refer to like parts and in which.

DETAILED DESCRIPTION OF THE PREFERRED EMBODIMENT

Figure 1:
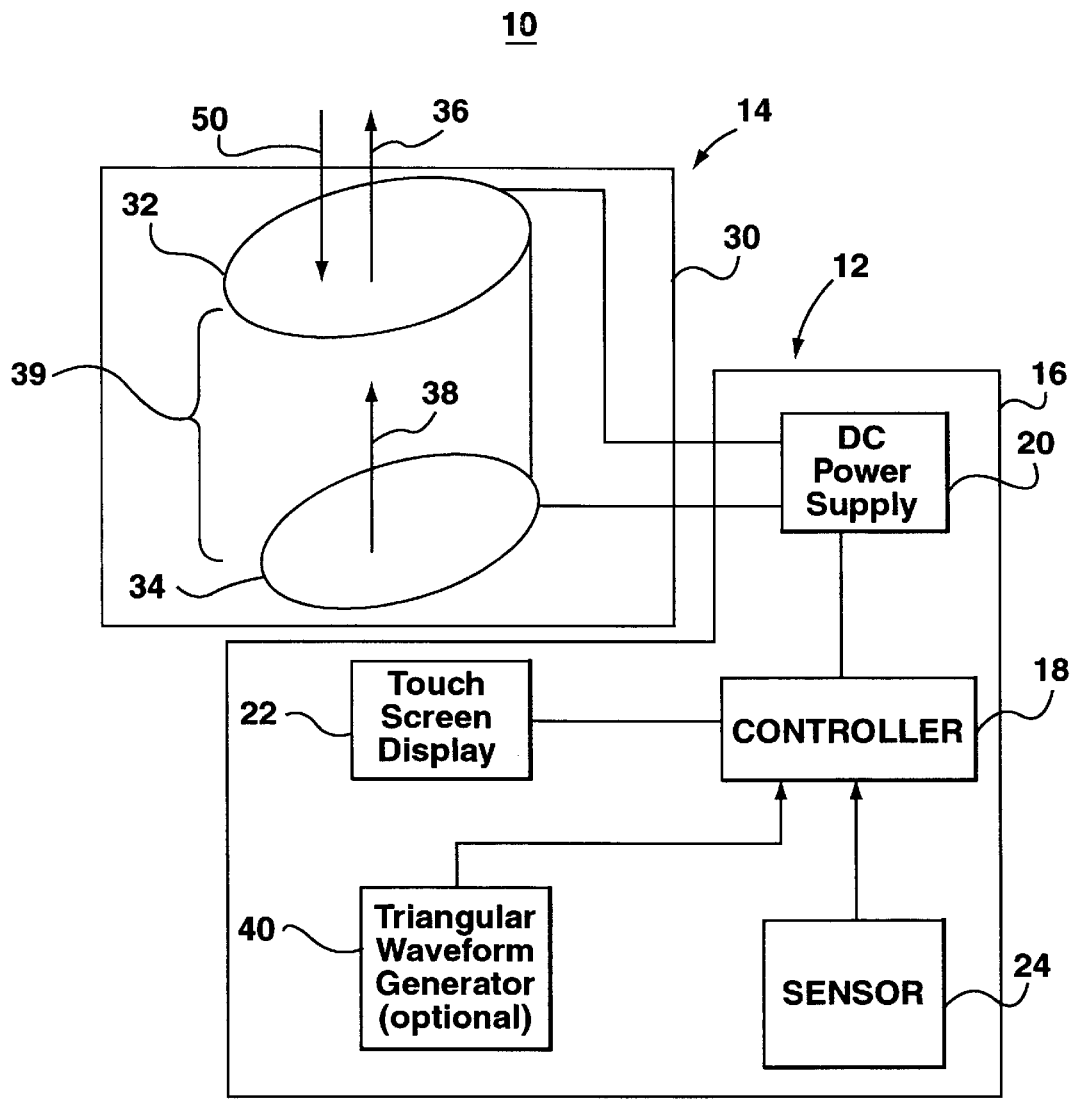
FIG. 1 is a schematic diagram of a therapeutic device made in accordance with the present invention.

Referring to FIG. 1, illustrated therein is a first embodiment of the subject invention. The therapeutic device, shown generally as 10, typically comprises a base unit 12 and a magnetic field generator assembly 14 operationally coupled to the base unit 12.

The magnetic field generator assembly 14 includes a head assembly housing or frame 30 to which are mounted two air cored coils, an upper coil 32, and a lower coil 34. The coils 32, 34 are electrically coupled such that current flows from one coil to the other.

As will be understood by one skilled in the art, each air cored coil 32, 34 is made of copper or any other suitably conductive wire which is laid out in concentric loops or "turns", forming a short cylindrical coil. When electric current is passed through such a coil, a magnetic field is generated which emanates from the wire in the coil. The direction of the current flowing through the wiring and the mechanical axis of the coil determines the orientation or direction of the generated magnetic field. The direction of the generated magnetic field (as illustrated by vectors 36, 38 with respect to the upper coil 32 and lower coil 34, respectively) is parallel to the longitudinal axis of each coil's 32, 34 cylinder. Alternatively, the coils 32, 34 may be concentrically wound or Archimedes coils.

The strength and shape of the magnetic field generated by air cored coils and other types of magnetic field generating coils (such as ferrite core and other permeable core materials) are affected by the strength of the current passing through the coil, as well as the shape and diameter of the coil. The number of turns in the coil also affect the strength and shape of the generated magnetic field. Although the coils 32, 34 are illustrated in FIG. 1 as being generally circular, as will be understood, the coils 32, 34 may be of different shapes such as squares, rectangles, triangles, octagons or freeform loops.

The coils 32, 34 are displaced from each other (forming a gap or zone 39), and preferably with their longitudinal axes substantially in alignment. In order to generate a relatively uniform magnetic field in the zone 39, if the coils 32, 34 are of similar dimension, the distance between the coils should approximate the radius of the coils 32, 34, resulting in a helmholtz coil configuration. As will be understood, the power supplied to the coils 32, 34, should be sufficient such that the magnetic fields generated by each coil 32, 34 overlap extensively within the zone 39. As well, preferably the zone 39 will be sufficiently sized to accommodate a substantial portion of a person's body (including his or her head). Although two coils 32, 34 are illustrated and described as being used in the generator assembly 14, alternatively, an appropriately configured and powered single coil may be used to generate an appropriate magnetic field. As well, more than two coils may be used to generate the desired magnetic field.

The base unit 12 typically includes a base unit housing 16 which holds a controller 18 (typically a suitably programmed CPU (central processing unit) having RAM (random access memory) and ROM (read only memory) operationally connected to a power source 20. Preferably, the device 10 also has a control data interface 22 such as a touch screen display operatively coupled to the controller 18 which displays operational data to the user and which receives input control instructions from the user to the controller 18. The controller 18 controls the operation of the device 10 and specifically the amount of current flowing from the power source 20 to the generator assembly 14. Alternatively, the controller 18 may comprise a manually adjustable switch or potentiometer to control the current flow.

As well, the base unit 12 also preferably includes a magnetic sensor 24 such as a magnetometer capable of detecting the strength of the local magnetic field in the vicinity of the device 10, as described in greater detail, below.

Typically, the power source 20 will be configured to provide direct current to the coils 32, 34 during operation, and will preferably comprise an electrical cord for connection to a standard electrical outlet, in such manner as would be understood by one skilled in the art. As well, the power source 20 is also preferably filtered to prevent ripples in the current supplied to the coils 32, 34. Ripples have been found to cause adverse effects for some individuals suffering neurological disorders. The base unit 12 may also comprise a waveform generator 40 which may be used to vary the current supplied by the power source 20 to the coils 32, 34 by generating triangular waveforms. Alternatively, the generator 40 may comprise a pseudo-random or periodic frequency generator capable of generating waveforms used to drive the coils within the limits of the inductive frequency constraints imposed by the coils, as will be understood by one skilled in the art. However, acceptable results have been obtained without the use of a waveform generator.

While the local magnetic field may comprise various sources of magnetic fields (each having a potentially different orientation), such as high voltage power lines, and stellar activities such as sunspots, in general, the major component of the local magnetic field will be the earth's geomagnetic field, which in turn has a predominant component having an orientation or direction illustrated by vector 50.

The earth's geomagnetic field may be described as a vector having both amplitude and direction. Daily or "diurnal" variations of between 10 nT (nanotesla; note 1 nT=1 gamma) and greater than 100 nT often occur. These variations may result from the southward movement of the northern aural oval in the northern hemisphere or the northward movement of the southern aural oval in the southern hemisphere. Solar winds can also affect such variations based on their intensity and the level of the ionosphere. Micropulsations, short, spiky perturbations within the earth's magnetic field also occur. Sunspot activity can also create magnetic storms, generating large disturbances of hundreds and thousands of gammas of variation in the earth's field lasting from several minutes to hours and days. Such disturbances in the geomagnetic field can aggravate the symptoms of those suffering from health conditions involving neurological, endocrinal, or auto-immune disorders, such as Multiple Sclerosis, Guillain-Barre Syndrome, myotonic multiple dystrophy, migraine headaches and unipolar disorders.

In the Northern Hemisphere, the predominant component of the earth's geomagnetic field is vertical, pointing downwards towards the centre of the earth. By contrast, in the Southern Hemisphere, the vector of the geomagnetic field is reversed. At the North and South Poles, the geomagnetic field is essentially vertical, but becomes angled in relation to vertical (inclination or declination), until it is essentially horizontal at the equator.

As noted, in the Northern Hemisphere, the vector 50 will typically be vertical, pointing downwards (towards the centre of the earth). In order to generate a magnetic field capable of cancelling some or all of the local geomagnetic field, the coils 32, 34 are preferably aligned such that their longitudinal axes are substantially parallel to the direction of the predominant geomagnetic field component 50. The current supplied to the coils 32, 34 by the power source 20 flows in the direction required to generate magnetic fields having an orientation 36, 38 opposite to that of the geomagnetic field's predominant component 50.

In use, the sensor 24 detects the strength of the predominant component of the local magnetic field, and forwards data correlated to this strength to the controller 18. Using the touch screen display 22, the user is able to input data to the controller 18 correlated to the strength of the magnetic field the user wishes to be present in the zone 39, depending on the needs of the user. Alternatively, the user may simply manually adjust the power level to create a magnetic field that provides the most therapeutic benefit to the user.

In Toronto, Ontario, Canada, the earth's magnetic field is approximately 57,000 nT, and is somewhat off vertical with a 70° angle of inclination. For this region, it has been found that a resulting field within the zone 39 having the strength (and direction) between approximately −10,000 nT to approximately −30,000 nT provides beneficial results. To generate a resulting field in this range, the coils 32, 34 must be powered to generate approximately −67,000 nT to −87,000 nT. Specifically, a resulting field of approximately −24,000 nT as measured by a flux gate magnetometer at approximately head height in the zone 39, has resulted in particularly beneficial alleviation of symptoms.

However, the resulting magnetic field within the zone 39 can be generated to have any strength and direction that is of benefit to the user. The orientation of the resulting magnetic field can also be positive or negative depending on the user's requirements and the location where the device 10 is located.

The controller 18 then calculates the current to be supplied by the power supply 20 to the coils 32, 34 (and causes the power supply 20 to supply such calculated power) in order to generate a magnetic field of sufficient strength to cancel out some or all of the sensed local magnetic field or effectively reverse such magnetic field, such that the resulting magnetic field strength within the zone 39 approximates the desired level.

Alternatively, the user may simply manually adjust the voltage supplied to the coils 32, 34, until the resulting magnetic field within the zone 39 is most comfortable and effective for the user.

The user then positions himself or herself substantially within the zone 39 for a period of time sufficient to alleviate some of the symptoms of the neurological condition suffered by the user. When used herein, it should be understood that "a sufficient period of time" (and variations thereof) is intended to mean a period of time to provide the user with an appreciable reduction in the individual's symptoms. The period of time may vary from user to user, depending on the severity of the individual's symptoms and the strength of the local magnetic field, at the time. The period of time may also be affected by the strength of the resulting magnetic field within the zone 39. Typically, 1.5 to 2 hours (at a strength of approximately 24,000 nT opposite in direction to the predominant component of the local magnetic field within the zone 39) has been found to produce favourable results in this regard. In some cases, symptoms may be alleviated for days following use of the device 10. Some users experience relief from symptoms of health-related disorders within minutes of exposure within the zone 39.

The controller 18 may be programmed to initiate a magnetic field generation session for a period of time input by the user, or alternatively, the user may simply initiate and terminate a session manually. During operation, preferably the sensor 24 will detect any changes in the strength of the local magnetic field and the controller 18 will correspondingly vary the power supplied to the coils 32, 34, to maintain the resulting magnetic field within the zone 39 at the desired level.

The device 10 has been illustrated as utilizing air cored coils 32, 34 configured to generate a magnetic field having one orientation, to cancel out some or all of the predominant component of the earth's local geomagnetic field oriented in the opposite direction. However, in order to provide a zone in which magnetic fields oriented in directions other than that of the geomagnetic field (such as from high voltage power lines or stellar activities) are altered, it would be possible to configure three sets of coils (with at least one coil in each set) such that the coil(s) in each set had a longitudinal axis orthogonal to the longitudinal axis of the coil(s) in each of the other two sets. Magnetic fields could then be generated along orthogonal X, Y and Z axes. Each set of coils would be independently powered, and a triaxial magnetometer sensor would be used to determine the strength of magnetic fields in the direction of each of the X, Y and Z axes. The controller would then be configured to modify the voltage (and direction of current) provided to each set of coils to cancel some or all of the local magnetic field in each of the X, Y and Z axes.

Figure 2:
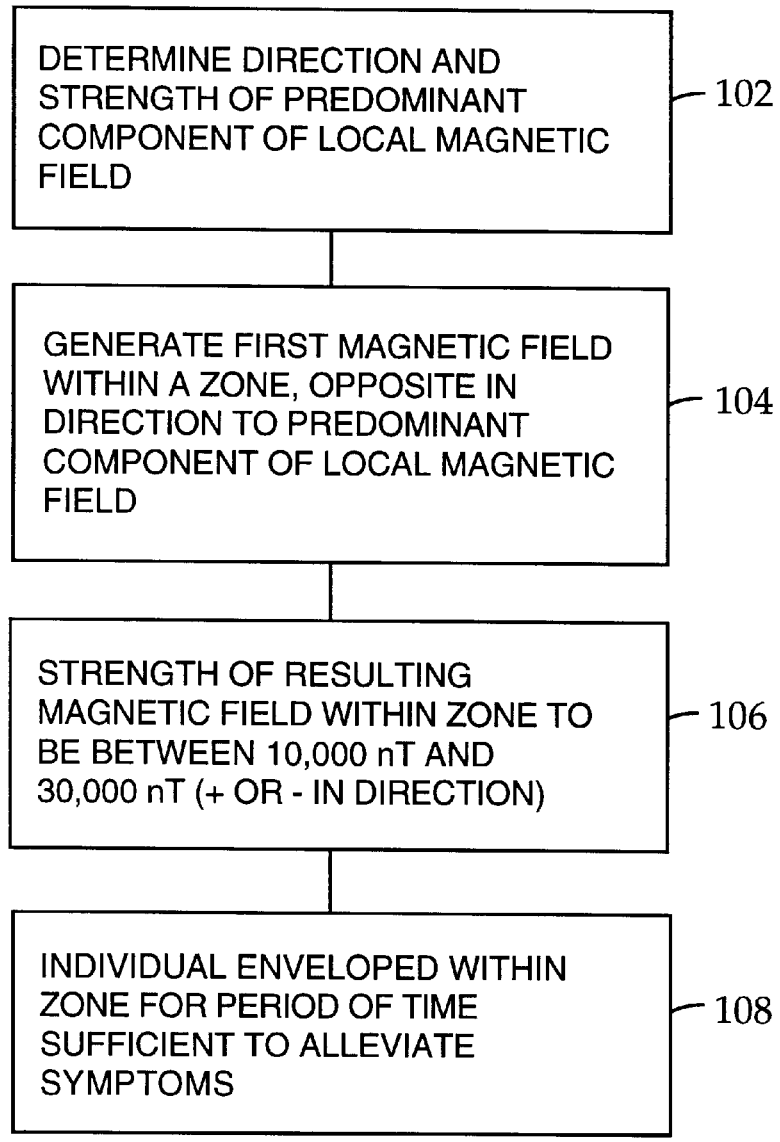
FIG. 2 is a flow diagram of the preferred method of the subject invention.

FIG. 2 illustrates the steps of the method 100 of alleviating symptoms of health related disorders, in accordance with the subject invention. The direction and strength of the predominant component of the local magnetic field are determined. (Block 102) Typically, the individual suffering the disorder is seeking relief from the geomagnetic field, the predominant component of which is vertical (in the Northern and Southern Hemispheres). The strength of this predominant component may be approximated from information sources such as geomagnetic maps and charts which track the geomagnetic field around the world. More preferably, a sensor will be used to detect the strength and direction of the geomagnetic field where the user is located.

A first magnetic field is then generated to create a zone. The first magnetic field is opposite in orientation to the field from which the user is to be shielded. (Block 104) Within the zone, the local magnetic field and the first magnetic field interact, creating a resulting magnetic field. Typically, properly configured air cored coils will be used, as discussed above, to create a zone which is large enough to envelop a significant portion of a person. When used herein, it should be understood that "a significant portion of a person" (and variations thereof) is intended to mean at least the person's head and torso. Preferably, the person's entire body will be enveloped within the zone.

The current supplied to the coils to generate the first magnetic field must have sufficient voltage such that the resulting magnetic field within the zone 39 has an absolute value (meaning independent of sign, + or −) between approximately 10,000 nT and 30,000 nT, opposite in direction to the orientation of the local magnetic field's predominant component. (Block 106) The user then positions himself or herself within the zone 39, for a period of time sufficient to alleviate the individual's symptoms. (Block 108) The user may also adjust the magnetic field generated by the coils such that the resulting magnetic field within the zone 39 is most beneficial to the user's particular needs.

Figure 3A:
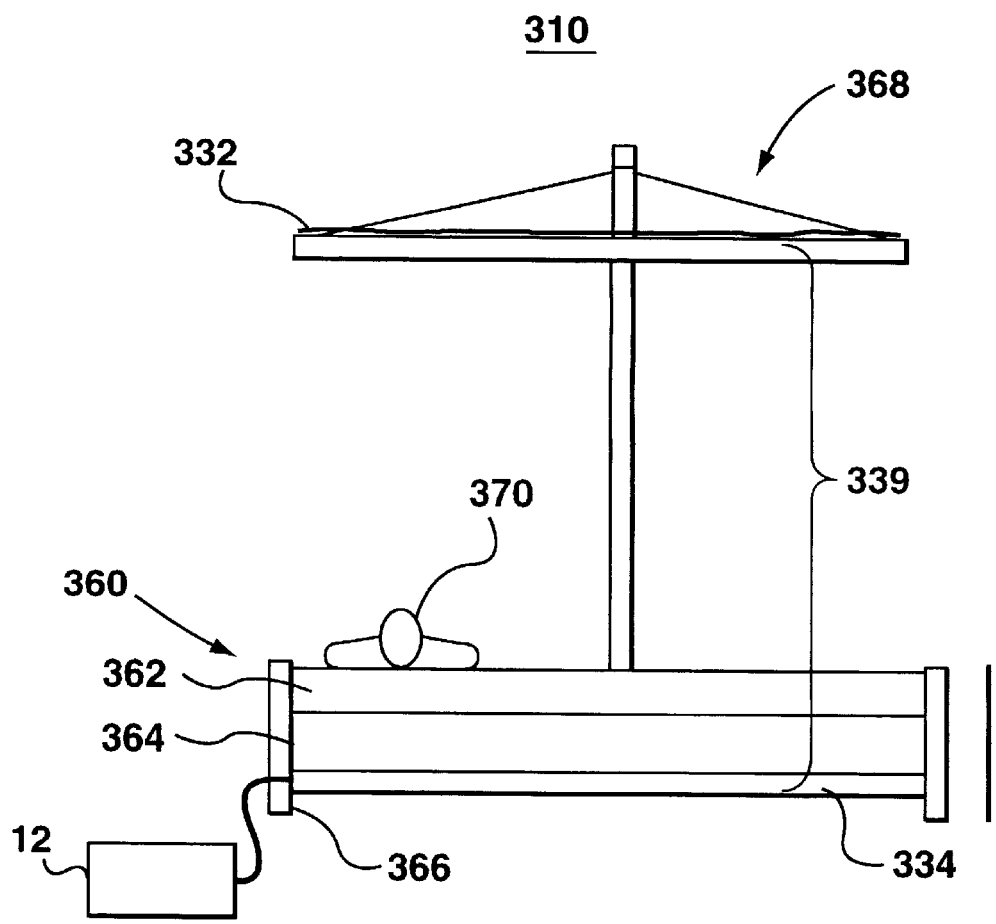
FIG. 3A is an end view of a therapeutic bed embodiment of the present invention.
Figure 3B:
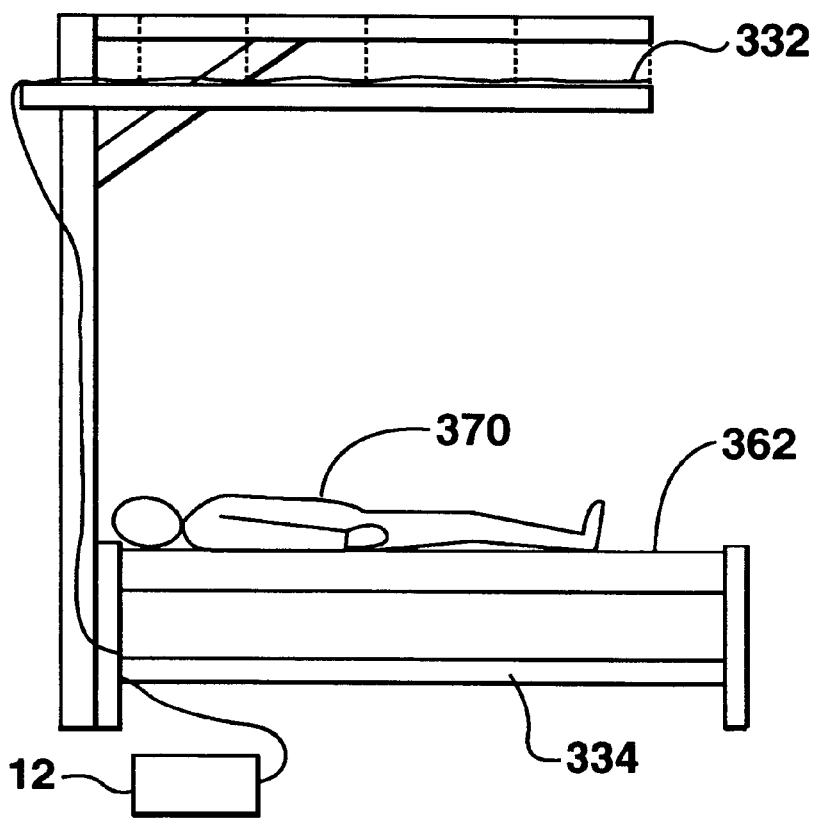
FIG. 3B is a side view of the therapeutic bed device of FIG. 3A.

An embodiment of the therapeutic device 310 configured with a bed is illustrated in FIGS. 3A and 3B. The device 310 is generally similar to the device 10 illustrated in and described with respect to FIG. 1, and includes a base unit 12. The device 310 includes a bed 360 having a mattress 362, box spring 364, bed frame 366 and canopy 368. As will be understood, different styles of bed may be used.

An upper air cored coil 332 is positioned about the periphery of the canopy 368, in a generally rectangular shape. A lower air cored coil 334, also substantially rectangular in shape, is positioned at the base of, and substantially follows the periphery of, the bed 360. A user 370 is shown lying on top of the mattress 362, in the zone 339 between the coils 332, 334.

Figure 4A:
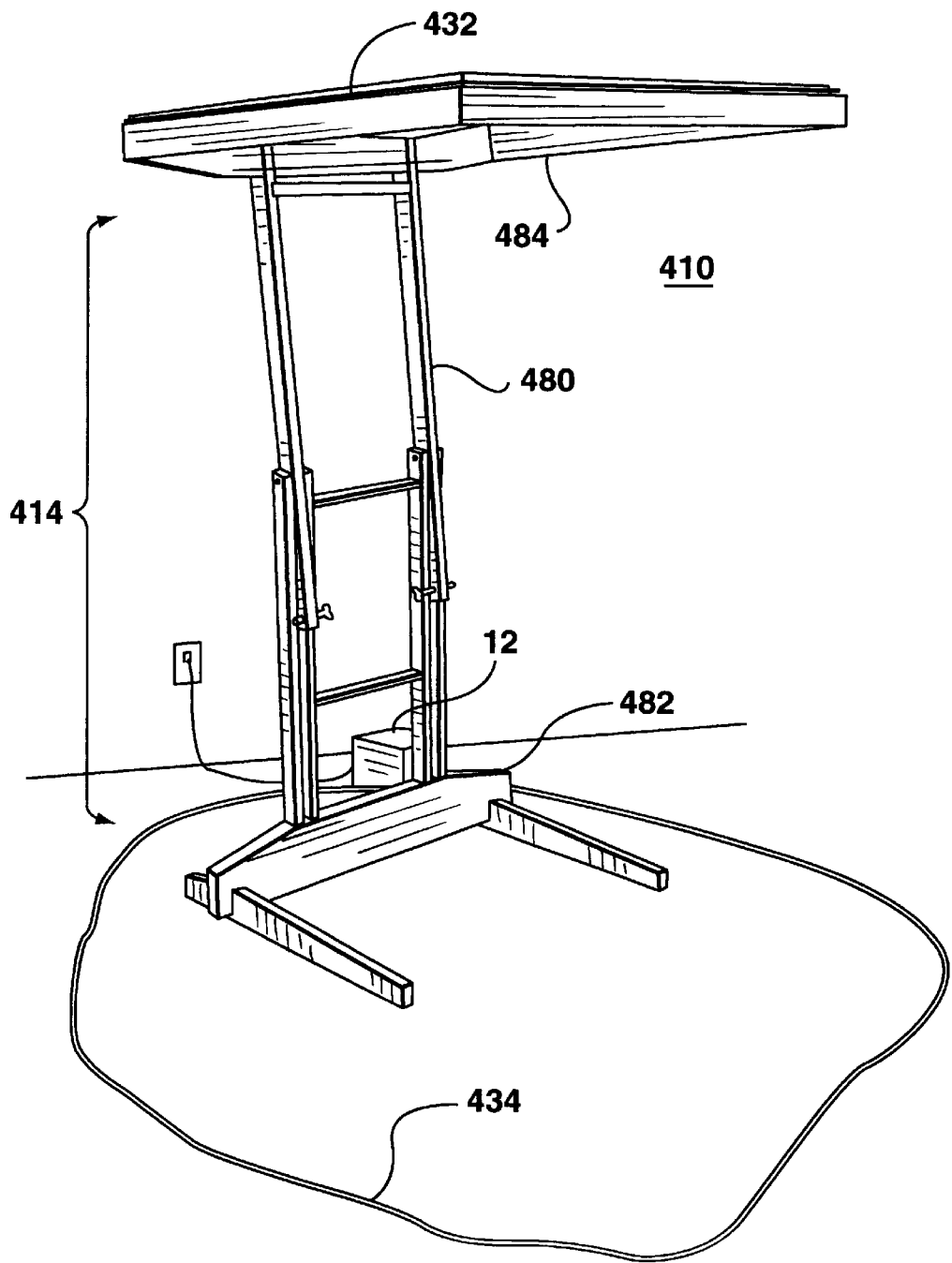
FIG. 4A is a front perspective view of a second embodiment of the present invention.
Figure 4B:
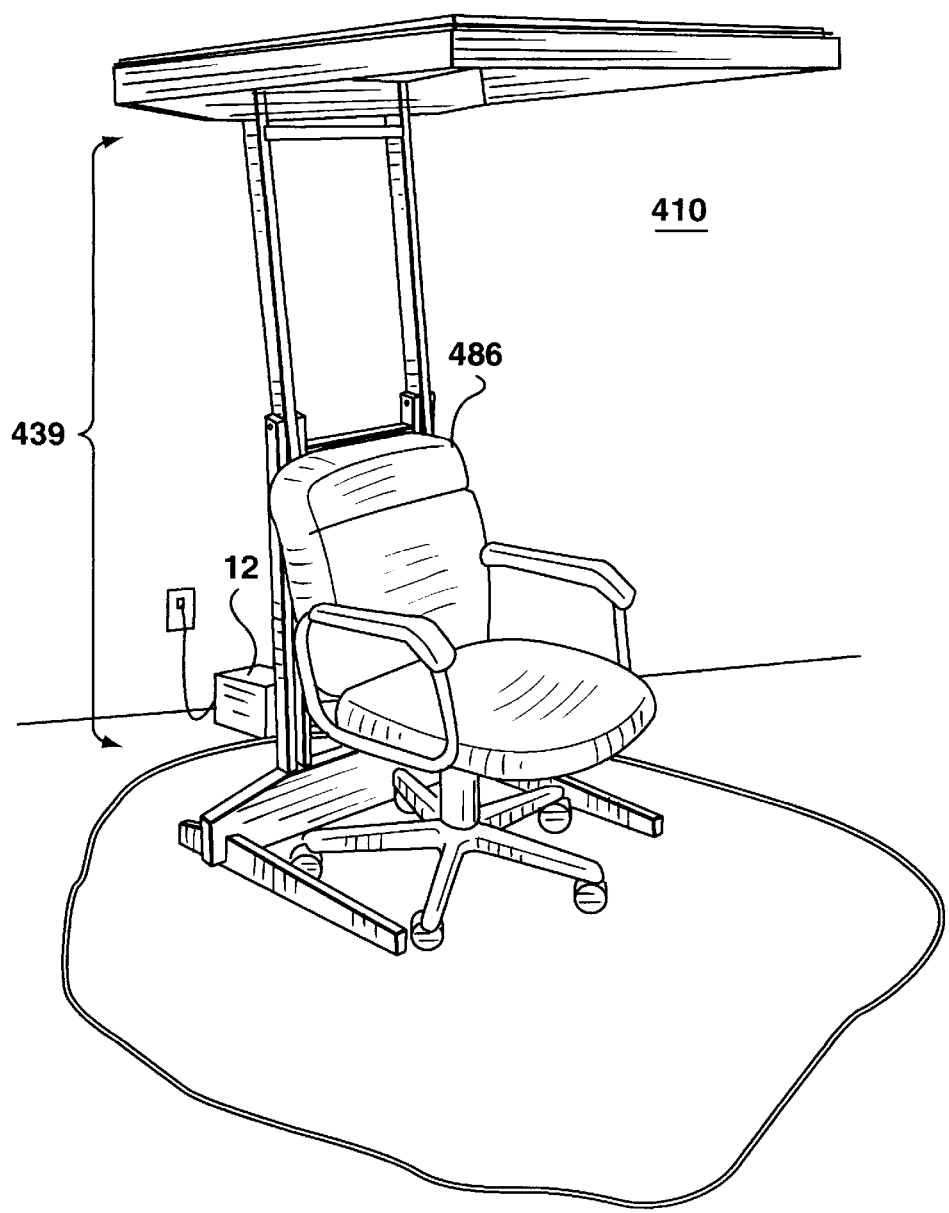
FIG. 4B is a front perspective view of the therapeutic device of FIG. 4A with a chair positioned in the zone between the upper and lower helmholtz coils.

A second embodiment of the therapeutic device 410 generally for use with a chair is illustrated in FIGS. 4A and 4B. The device 410 is generally similar to the device 10 illustrated in and described with respect to FIG. 1, and includes the base unit 12. The generator assembly 414 includes a frame 480 having a base 482 and an upper, generally rectangular, halo assembly 484. An upper air cored coil 432 is mounted to the halo assembly 484, generally matching the assembly's 484 periphery, while a lower air cored coil 434 is set out in a roughly circular loop on the floor about the base 482 of the frame 480. As shown in FIG. 4B, a chair 486 or other piece of furniture such as a bed may be positioned in the zone 439 between the coils 432, 434. Alternatively, the chair 486 may be mounted to the frame 480.

Because of the proximity of the user's lower torso, legs and feet with respect to the lower coil 434, it is preferable for this coil 434 to be configured to create a reduced magnetic field than the upper coil 432. Having the lower coil 434 enclose a surface area approximately 2.7 times larger than that of the upper coil 432 has been found to produce acceptable results in this regard. As well, preferably the upper coil 432 has triple the number of turns than the lower coil 434. Other turns ratios and coil dimension configurations may also produce acceptable results.

It is important that the resulting magnetic field generated within the zone not be too powerful. For individuals suffering certain disorders such as MS, a resulting field which is too strong may actually create or exacerbate disorder symptoms.

Figure 5A:
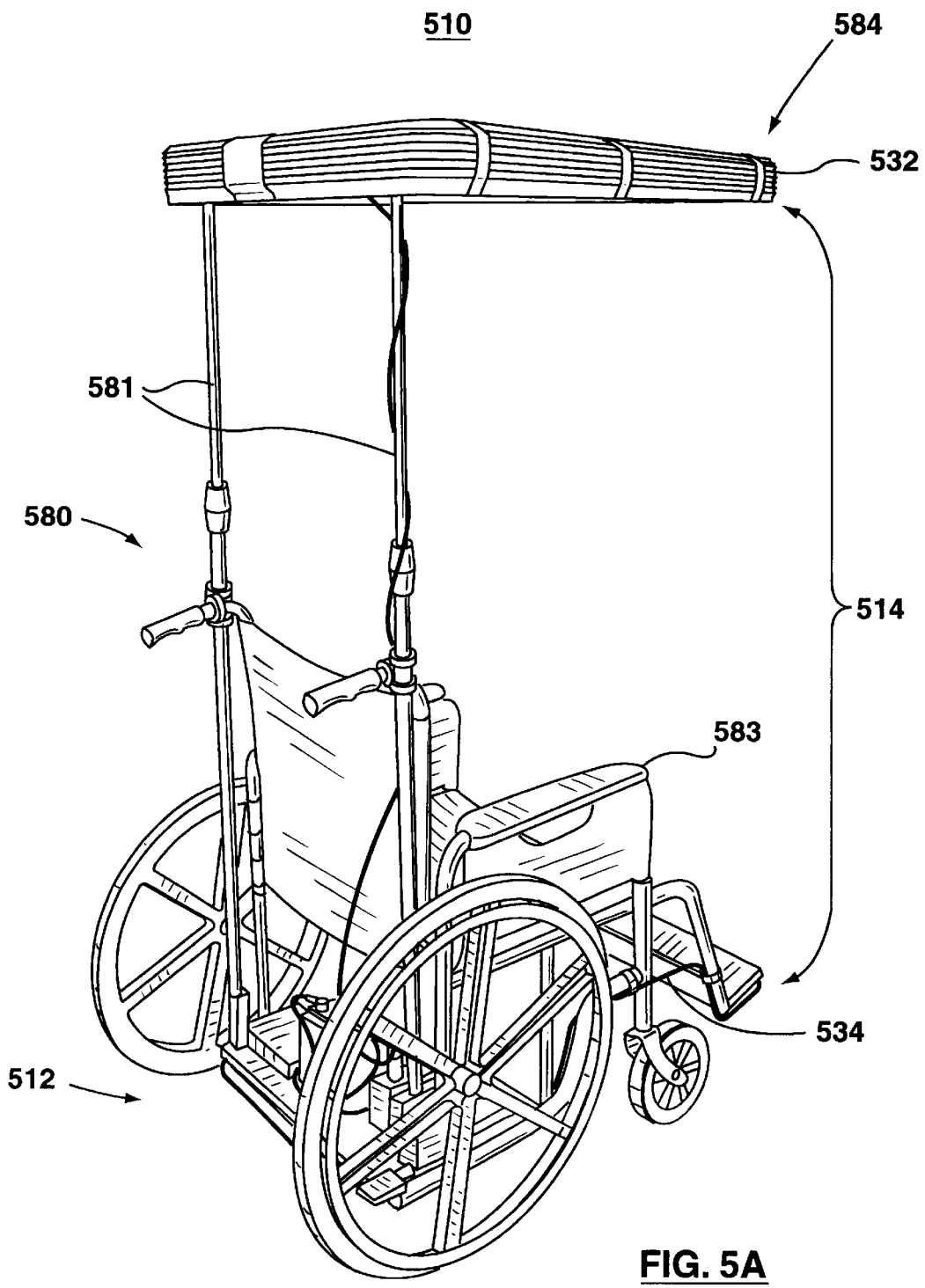
FIG. 5A is a rear perspective view of a third embodiment of the present invention, namely a wheelchair equipped with a therapeutic device.
Figure 5B:
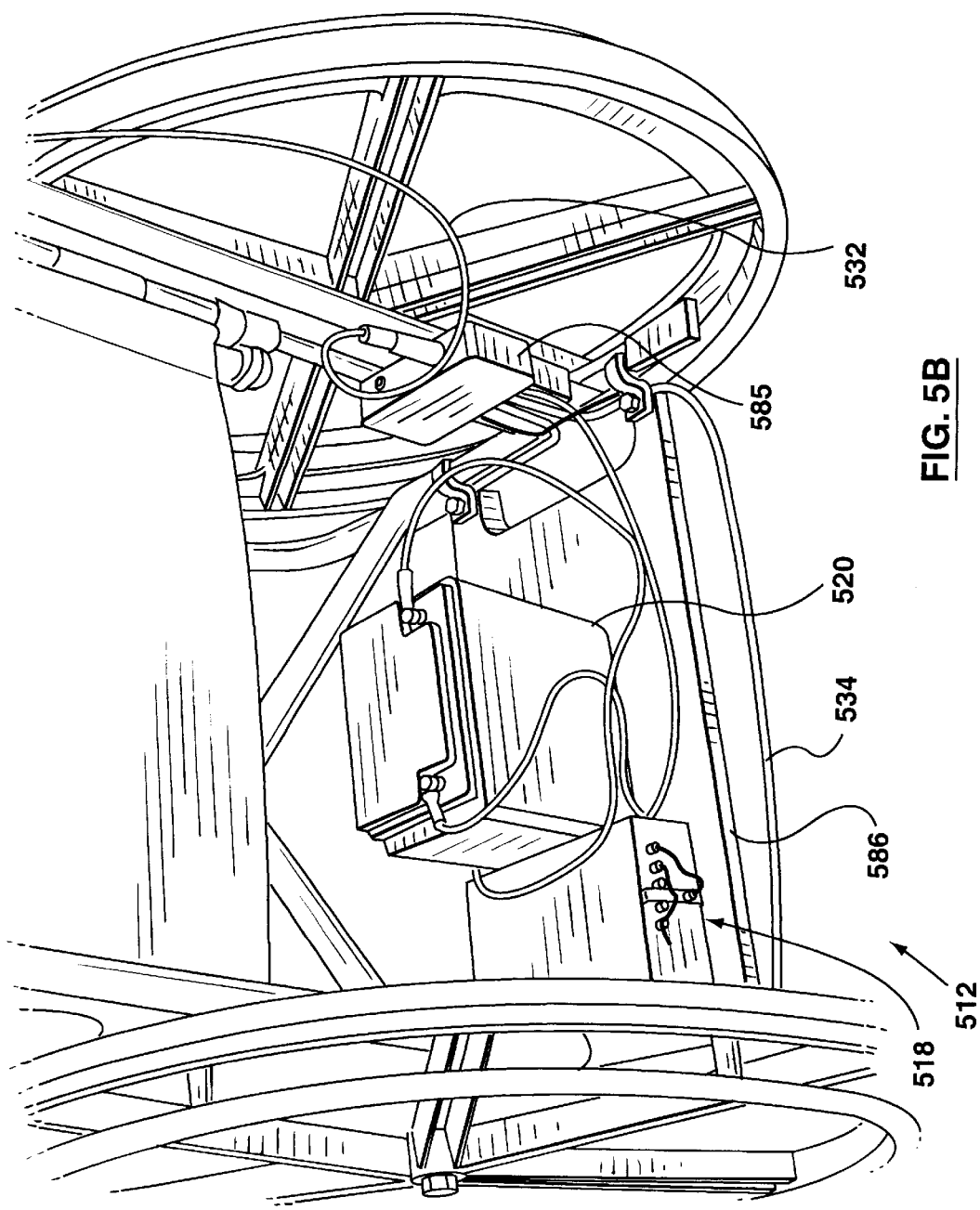
FIG. 5B is a rear perspective view of the base unit components of the device of FIG. 5A.

A third embodiment of the therapeutic device, namely a wheelchair equipped with a therapeutic device 510 is illustrated in FIGS. 5A and 5B. The device 510 is generally similar to the device 10 illustrated in and described with respect to FIG. 1, and includes a base unit 512 and a magnetic field generator assembly 514.

The generator assembly 514 includes a frame 580 having adjustable supports 581 mounted to the rear of a wheelchair 583 (typically to the push handles and to the undercarriage) and an upper, generally square and horizontal halo assembly 584. Generally each side of the halo assembly 584 is approximately two feet in length. An upper air cored coil 532 is mounted to the halo assembly 584, generally matching the assembly's 584 periphery. The height of the upper coil 532 can be varied to suit the user, using the adjustable supports 581. The supports 581 are preferably made of aluminum (for light weight) or other sturdy metal, capable of supporting the halo 584 when the wheelchair 583 is subjected to rigorous activity. Preferably, the halo assembly 584 is detachable from the adjustable supports 581, to enable the wheelchair 583 to be folded up for storage or transportation. Once the halo assembly 584 has been detached, the supports 581 can be lowered to their minimum height when the wheelchair 583 is collapsed.

As shown in FIG. 5B, the upper coil 532 is electrically detachably coupled to a juncture box 585 mounted to the lower undercarriage of the wheelchair 583. The upper coil 532 may be made from heavy duty insulated copper magnet wire since it does not require a significant amount of flexibility in order to be detachable from the juncture box 585, when the wheelchair 583 is to be collapsed. An upper coil 532 having one hundred and forty-four turns has been found to produce acceptable results.

A lower platform 586 is also provided, which is mounted to the undercarriage of the wheelchair 583, beneath the seat portion of the wheelchair 583. The platform 586 carries the base unit 512 components. Preferably, the platform 586 is detachable from the undercarriage, to enable the wheelchair 583 to be folded up for storage or transportation. Preferably, the base unit 512 also includes a waterproof housing (not shown) to protect the base unit 512 components.

The base unit 512 comprises power supply 520, electrically coupled to a controller 518, and to the generator assembly 514. Preferably the power supply 520 includes a rechargeable 12 volt direct current battery, of the gel/cell type which cannot be spilled in any orientation. In general, the controller 518 is similar to the controller 18 illustrated in and described in relation to FIG. 1. The controller 518 will also include a touch screen display or other input device for enabling a user to adjust the amount of current provided by the power supply 520 to the generator assembly 514. Preferably, the base unit 512 also includes a battery charger which can recharge the power supply 520 by plugging the battery charger into a standard electrical socket. Additionally, the base unit 512 also includes an alert mechanism electrically coupled to the power supply 520, for indicating to the user when the power supply 520 is running low.

Typically the alert mechanism will generate an audible tone or a flashing light which the user can detect and will recognize.

The generator assembly 514 also includes a lower air cored coil 534 set out in a generally horizontal loop mounted to the undercarriage of the wheelchair 583, substantially beneath the seat. The lower coil 534 is electrically coupled to the juncture box 585. In general, the lower coil runs across the back, down the sides and across the front, of the wheelchair 583. The lower coil 534 preferably mounts to and crosses between the footrests of the wheelchair 583. It is important that the lower coil 534 be positioned to avoid obstructing the wheels of the wheelchair 583 (particularly the front swivel wheels). The lower coil 534 should preferably be flexible to enable it to follow the contours of the undercarriage support structure to which it is mounted, and also to allow it to bend when the wheelchair 583 is collapsed. Accordingly, the lower coil 534 may be made from multiconductor cable using stranded and tinned copper wire, which is relatively durable.

As well, providing the lower coil 534 with 25 turns has been found to produce acceptable results. As a result, the turns ratio between the upper coil 532 and the lower coil 534 is approximately six to one. Preferably, the resulting field strength near the lower coil 534 is maintained at an absolute value of approximately 25,000 nT (ie. 25,000 nT or −25,000 nT, depending on the location of the device 510 and the direction of the field, as will be understood), because of the proximity of the user's feet to the lower coil.

Although the wheelchair 583 has been illustrated and described as being a standard manual powered wheelchair, it should be understood that the device 510 can be adapted to comprise an electric wheelchair or various other types of wheelchair devices.

Thus, while what is shown and described herein constitute preferred embodiments of the subject invention, it should be understood that various changes can be made without departing from the subject invention, the scope of which is defined in the appended claims.

We claim:

1. A method of alleviating the symptoms of health-related disorders, the method comprising the steps of:
   (a) determining the direction and strength of a predominant component of a local magnetic field;
   (b) generating a first magnetic field within a zone, wherein the generated magnetic field is approximately opposite in direction to the predominant component of the local magnetic field;
   (c) wherein the first magnetic field is of sufficient strength such that within the zone the strength of the resulting magnetic field has an absolute value between approximately 10,000 nT and 30,000 nT; and (d) positioning an individual having health-related disorder symptoms substantially within the zone for a sufficient period of time to alleviate the individual's symptoms.

2. The method as claimed in claim 1, wherein step (a) comprises sensing the strength of the predominant component.

3. The method as claimed in claim 1, wherein step (b) comprises varying the strength of the first magnetic field in accordance with detected changes in the sensed local magnetic field.

4. The method as claimed in claim 1, wherein the health-related disorder is selected from the group consisting of: neurological disorders, endocrine disorders and autoimmune disorders.

5. The method as claimed in claim 1, wherein the health-related disorder is selected from the group consisting of: Multiple Sclerosis, Guillain-Barre Syndrome, myotonic multiple dystrophy, unipolar disorders and migraine headaches.

6. The method as claimed in claim 1, wherein step (a) comprises sensing the direction of the predominant component.

7. The method as claimed in claim 1, further comprising the step of varying the strength of the first magnetic field to maximize the alleviation of symptoms for the individual.

* * * * *